United States Patent [19]

Howe et al.

[11] 4,298,375

[45] Nov. 3, 1981

[54] 2-SUBSTITUTED-5-PHENYL-4-THIAZOLECARBOXYLIC ACIDS AND THEIR DERIVATIVES AS SAFENING AGENTS

[75] Inventors: Robert K. Howe, Bridgeton; Len F. Lee, Maryland Heights, both of Mo.

[73] Assignee: Monsanto Company, St. Louis, Mo.

[21] Appl. No.: 80,749

[22] Filed: Oct. 1, 1979

[51] Int. Cl.³ ............................................. C07D 277/20
[52] U.S. Cl. ........................................... 71/90; 71/100; 71/118; 548/184; 548/188; 548/194
[58] Field of Search ............................ 71/118, 90, 100; 548/184, 188, 194

[56] References Cited

U.S. PATENT DOCUMENTS

| | | | |
|---|---|---|---|
| 2,500,142 | 3/1950 | Wiesehahn | 260/302 |
| 3,536,727 | 10/1970 | Cavalla et al. | 260/302 |
| 3,775,425 | 11/1973 | Bosshard et al. | 71/90 |
| 3,833,601 | 9/1974 | Beck et al. | 260/302 R |
| 3,874,873 | 4/1975 | Volpp et al. | 71/90 |
| 4,153,703 | 5/1979 | Harrison et al. | 424/270 |

FOREIGN PATENT DOCUMENTS 1187620 2/1965 Fed. Rep. of Germany.
1532240 11/1978 United Kingdom.

OTHER PUBLICATIONS

CA vol. 40 4056–4061 (1946).
CA vol. 42 2969 (1948).
CA vol. 54 22576 (1960).
CA vol. 58 4534 (1963).

*Primary Examiner*—Nicholas S. Rizzo
*Attorney, Agent, or Firm*—Patricia A. Coburn; Donald W. Peterson

[57] ABSTRACT

2-Substituted-5-phenyl-4-thiazolecarboxylic acids and their derivatives have been found to be effective in reducing herbicidal injury to sorghum plants caused by triallate, alachlor and butachlor herbicides, and especially in reducing herbicidal injury to sorghum plants caused by alachlor herbicide.

32 Claims, No Drawings

2-SUBSTITUTED-5-PHENYL-4-THIAZOLECARBOXYLIC ACIDS AND THEIR DERIVATIVES AS SAFENING AGENTS

This invention relates to novel 2-substituted-5-phenyl-4-thiazolecarboxylic acids and derivatives thereof as well as their use in compositions and methods for reducing herbicidal injury. More specifially, the invention relates to novel compositions and methods for reducing injury to sorghum by S-(2,3-dichloroallyl)diisopropylthiocarbamate, 2-chloro-2',6'-diethyl-N-(methoxymethyl)acetanilide and 2-chloro-2',6'diethyl-N-(butoxymethyl)acetanilide (hereinafter referred to by their common names as, respectively, triallate, alachlor and butachlor) which comprises treating the sorghum plant locus or the seed of the sorghum plant with an effective amount of a 2-substituted-5-phenyl-4-thiazolecarboxylic acid or derivative thereof which will be described more fully below.

BACKGROUND OF THE INVENTION

Triallate, alachlor and butachlor are very useful for controlling weeds in the presence of growing crops. Application of these herbicides to sorghum at rates necessary to kill or stunt weeds, however, injures the sorghum plant, slowing growth and development. Accordingly, the use of these herbicides to control weeds in the presence of sorghum is rendered less desirable. Obviously, a safening agent consisting of a chemical compound that could be used to treat either the seed of the sorghum plant, the sorghum plant locus, or the sorghum plant itself, such that a reduction of injury due to application of the herbicide without a corresponding reduction of herbicidal action on the weed, would be quite beneficial.

DESCRIPTION OF THE INVENTION

In accordance with the novel aspects of the present invention, injury to sorghum due to application thereto of triallate, alachlor and butachlor herbicides, and especially alachlor herbicide, may be reduced, without a corresponding reduction in injury to the weeds, by application to the sorghum plant locus or the seed of the sorghum plant prior to planting, of an effective amount of a safening agent comprising a 2-substituted-5-phenyl-4-thiazolecarboxylic acid, or derivative thereof, having the formula

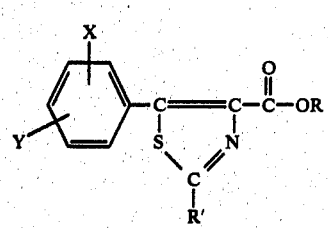

wherein R is hydrogen, lower alkyl, halo(lower)alkyl, lower alkenyl, halo(lower)alkenyl or agriculturally acceptable cations; R' is halo, amino, lower alkoxy or phenylthio. X and Y independently equal hydrogen, lower alkyl, lower alkoxy, trifluoromethyl or halo moieties.

As used herein, the term "lower alkyl", "lower alkoxy" or "halo(lower)alkyl" is understood to include alkyl or alkoxy groups having up to five carbon atoms, inclusive.

The term "alkyl" is understood to include branched, unbranched and cyclic alkyl groups.

The term "halo(lower)alkyl" is used herein to refer to a monohalo substituted alkyl group containing 1 to b 5 carbon atoms as, for example, chloromethyl, chloroethyl, bromomethyl and the like.

Where the expression "lower" is employed in conjunction with the term "alkenyl" or "halo alkenyl" it is intended to indicate that the alkenyl portion of the substituent group has a carbon content of 2 to 5 carbon atoms and preferably 3 to 5 carbon atoms and most preferably 3 carbon atoms. Typically alkenyl includes such groups as ethenyl, 1-propenyl, 2-propenyl, 1-methyl-2-propenyl, 2-methyl-2-propenyl, 2-butenyl, 1-methyl-3-butenyl and the like.

"Halogen" includes bromine, chlorine, fluorine and iodine. The chlorine atom is preferred for use herein.

The term "amino" refers to the —NH₂ substituent group.

The term "phenylthio" refers to the

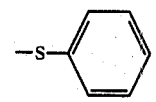

substituent group.

By the term "agriculturally acceptable cations" is meant those cations that are commonly used to form the salt of the free acid. Such cations include, but are not limited to, alkali metal, alkaline earth, substituted amine and ammonium cations. Preferred for use herein are the sodium and potassium salts. There are very large numbers of agriculturally acceptable cations suitable for use in this invention as would readily be appreciated by one skilled in the art.

Preferred for use herein are those safening agents of the foregoing formula in which R is methyl and R' is chloro, amino, methoxy or phenylthio and X and Y are hydrogen.

Safening agents useful in accordance with the present invention include, but are not limited to, methyl 2-amino-5-phenyl-4-thiazolecarboxylate; methyl 2-chloro-5-phenyl-4-thiazolecarboxylate; methyl 2-methoxy-5-phenyl-4-thiazolecarboxylate and methyl 2-phenylthio-5-phenyl-4-thiazolecarboxylate.

Generally, the 2-substituted-5-phenyl-4-thiazolecarboxylates of the foregoing formula may be prepared by the following reaction scheme:

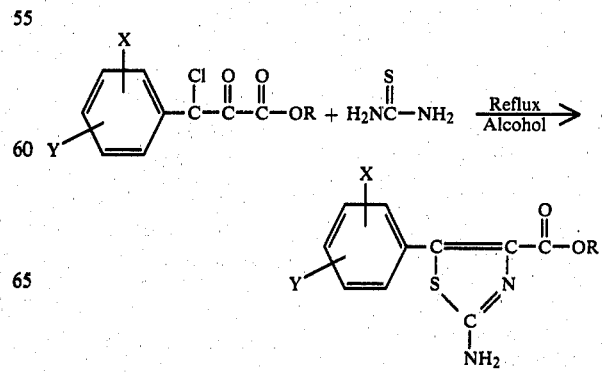

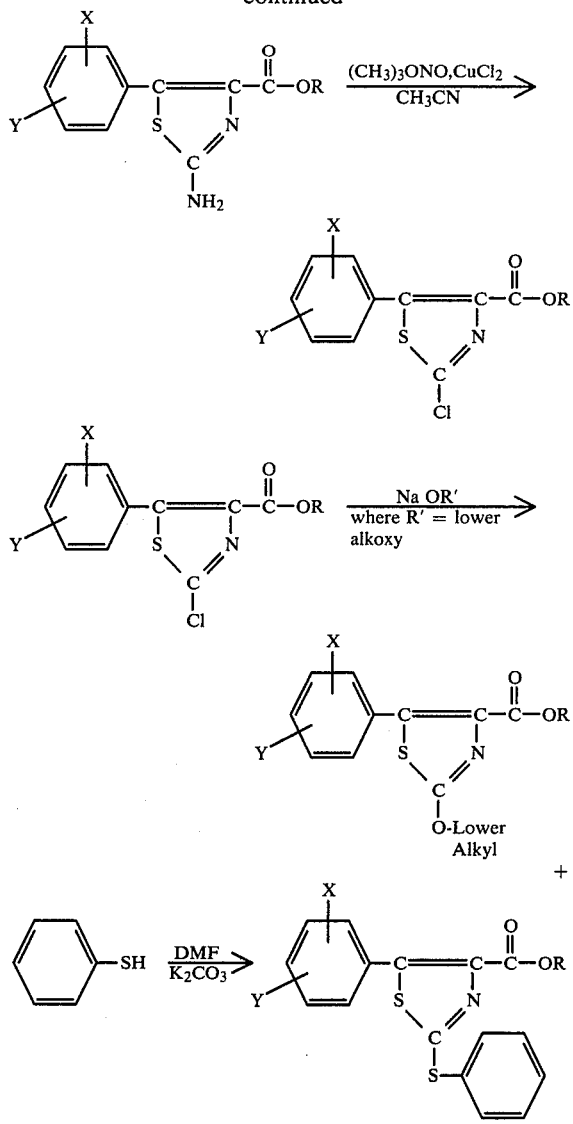

In accordance with the above scheme, chlorophenyl pyruvates are treated with thiourea in refluxing alcohol to yield the desired 2-amino-thiazoles. The amino group is then coverted into the chloro substituent in accordance with literature procedures (M. P. Doyle, et al, J. ORG CHEM, 42, 2426, 1977). The 2-chlorothiazoles can then be reacted with an alkoxide nucleophile, in alcohol, to yield the desired 2-alkoxy-thiazole or with phenylthiol in DMF treated with potassium carbonate to yield the 2-phenylthio derivative.

In order to more fully illustrate the above procedure the following examples are presented.

EXAMPLE 1

Preparation of Methyl 2-Amino-5-Phenyl-4-Thiazolecarboxylate. Methyl phenyl chloropyruvate, 107.5 gm (0.51 mol) was dissolved in methanol and the solution was added to a 2 liter, single necked round bottom flask and, thereafter, further methanol was added to bring the volume to 500 ml. To this solution was added 40.5 gm (0.53 mol) of thiourea with stirring. The resulting mixture was heated at reflux for 8 hours. The solvent was removed by rotary evaporation and the residue was then slurried in $H_2O$ and solid $K_2CO_3$ was added until the mixture was basic. Suction filtration yielded pale yellow crystals which were washed with cold $H_2O$ and methanol. The yellow crystals were boiled as a slurry in ethanol, cooled and filtered. The product, methyl 2-amino-5-phenyl-4-thiazole-carboxylate was obtained in 76% yield, m.p. 216°–217° C.

Anal. Calc'd for $C_{11}H_{10}$ $N_2O_2S$: C,56.40; H,4.30; N,11.96; S,13.45; Found: C,56.19; H,4.29; N,11.87; S,13.69.

EXAMPLE 2

Preparation of Methyl 2-Chloro-5-Phenyl-4-Thiazolecarboxylate. Under a static $N_2$ atm, a mechanically stirred mixture of $CuCl_2$ (0.12 mol, dried in an oven) and tert-butylnitrile (0.15 mol) in 200 ml of acetonitrile (distilled from $P_2O_5$) was treated in several portions with the compound of Example 1, (0.1 mol) via a solid addition setup at ambient temperature. After the addition, the mixture was stirred at ambient temperature for ½ hour. The mixture was then treated with 10% HCl and extracted three times with ether. The ether extracts were washed with 10% HCl, dried over $MgSO_4$ and concentrated in vacuo. The crude product was Kugelrohr distilled at approximately 120° C. (1–2 mm Hg) to give a yellow oil which solidified on standing. The product, methyl 2-chloro-5-phenyl-4-thiazole carboxylate, melted at 63°–65° C., yield 58%.

Anal. Calc'd for $C_{11}H_8Cl$ $NO_2S$: C,52.08; H,31.8; N,5.52; Cl,13.97; S,12.64; Found: C,51.92; H,3.05; N,5.52; Cl,13.91; S,12.72.

EXAMPLE 3

Preparation of Methyl 2-Methoxy-5-Phenyl-4-Thiazolecarboxylate. Under a static $N_2$ atm, a stirred solution of the compound of Example 2 (8.14 g, 32 mol) in 100 ml of methanol was treated dropwise with 7.6 g of 25% sodium methoxide in methanol. After stirring at ambient temperature for 24 hr, the mixture was added to $H_2O$ and extracted twice with ether. The ether layer was washed with $H_2O$, dried over $MgSO_4$ and concentrated in vacuo to yield a white solid which was recrystallized from methylcyclohexane to yield 5.5 g of methyl 2-methoxy-5-phenyl-4-thiazolecarboxylate as a white solid, m.p. 86°–88° C., yield 70%.

Anal. Calc'd. for $C_{12}H_{11}$ $NO_3S$: C,57.82; H,4.45; N,5.62; S,12.86. Found: C,57.73; H,4.37; N,5.61; S,13.20.

EXAMPLE 4

Preparation of Methyl 5-Phenyl-2-Phenylthio-4-Thiazolecarboxylate. A stirred suspension of $K_2CO_3$ (4.15 g, 30 mol) in 100 ml of DMF was treated in one portion with thiophenol (1.65 g, 15 mol). The compound of Example 2 (3.8 g, 15 mol) was then added and the mixture heated at 110° C.±5° C. for 2 days. Water was added and the mixture extracted twice with ether. The ether extracts were washed with $H_2O$, dried over $MgSO_4$ and concentrated in vacuo to yield a yellow oil. Bulb to bulb distillation yielded methyl 5-phenyl-2-phenylthio-4-thiazolecarboxylate, as a yellow oil at 130°–170° C./1 mm. This oil was crystallized from etherpetroleum ether mixtures to yield 1.6 g of white crystals, methyl 5-phenyl-2-phenylthio-4-thiazolecarboxylate, m.p. 67°–70° C., yield 33%.

Anal. Calc'd for $C_{17}H_{13}$ $NO_2S_2$: C,63.36; H,4.00; N,4.28; S,19.56; Found: C,62.01; H,3.83; N,4.41; S,19.78.

In accordance with the novel aspects of the present invention, the 2-substituted-5-phenyl-4-thiazolecarboxylates are useful for reducing herbicidal injury to sorghum plants, caused by triallate, alachlor and butachlor herbicides. The compounds of the present invention are preferentially employed as safeners for alachor herbicide in sorghum.

The amount of safening agent employed in the method and compositions of the invention will vary depending upon the manner of application, rate of application, environmental factors as well as other factors known in the art. In each instance, the amount employed is a safening effective amount, i.e., the amount which reduces crop injury by the herbicide.

The safening agent may be applied to the plant locus in a mixture with the herbicide or it may be applied directly to the sorghum seed itself. By application to the "plant locus" is meant application to the plant growing medium, such as the soil, as well as the seeds, emerging seedlings, roots, stems, leaves, flowers, fruits or other plant parts.

To illustrate the effectiveness of the 2-substituted-5-phenyl-4-thiazolecarboxylates of this invention the following examples are presented. These examples are presented merely as being illustrative of the novel aspects of the invention and are not intended to be a limitation as to the scope thereof.

EXAMPLE 5

A good grade of top soil is placed in a container and compacted to a depth of approximately 1.27 cm. from the top of said container. A predetermined number of sorghum seeds to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of triallate, alachlor or butachlor herbicide dispersed or dissolved in a suitable carrier is then sprayed on the soil already treated with the safening agent. The soil containing the safening agent and the herbicide is thoroughly mixed. This mixing is sometimes referred to as incorporation of the herbicide and safening agent into the soil. The mixing or incorporation provides a substantially uniform distribution of the safening agent and herbicide throughout the soil. The sorghum seeds are covered with the soil containing the safening agent and herbicide and the pans are leveled. The pans are then placed on a sand bench in the greenhouse and watered from below as needed. The sorghum plants are observed at the end of approximately 21 days and the results in terms of percent inhibition of each seed lot are recorded. For each test series a pan of plants is also prepared containing no herbicide and no safening agent as a control. Additionally, for each test, a pan of plants is prepared with soil covering the seed containing no herbicide and only the measured amount of safening agent being incorporated into the soil covering the seeds to ascertain any herbicidal effect of the safening agent alone. For each series of tests the herbicidal effect of the herbicide is observed from pans of sorghum plants tested with the same quantity of herbicide alone.

The "safening effect" is determined by adding the herbicidal effect of the herbicide when applied alone to the herbicidal effect of the safening agent when applied alone (in no instance, however, will this sum be greater than 100) and subtracting from that the herbicidal effect obtained when the herbicide and safening agent are incorporated into the soil as discussed above.

TABLE I

| Safening Agent (Compound of Example Number) | (Triallate) Rate of Safening Agent (kg/h) | Rate of Herbicide (kg/h) | Safening Effect |
|---|---|---|---|
| 1 | 8.96 | 0.56 | 56 |
| 2 | 8.96 | 0.56 | 45 |
| 3 | 8.96 | 0.56 | 37 |
| 4 | 8.96 | 0.56 | 35 |

TABLE II

| Safening Agent (Compound of Example Number) | (Alachlor) Rate of Safening Agent (kg/h) | Rate of Herbicide (kg/h) | Safening Effect |
|---|---|---|---|
| 1 | 8.96 | 2.24 | 24 |
| 2 | 8.96 | 2.24 | 20 |
| 3 | 8.96 | 2.24 | 23 |
| 4 | 8.96 | 2.24 | 20 |

TABLE III

| Safening Agent (Compound of Example Number) | (Butachlor) Rate of Safening Agent (kg/h) | Rate of Herbicide (kg/h) | Safening Effect |
|---|---|---|---|
| 1 | 8.96 | 6.72 | 35 |
| 2 | 8.96 | 6.72 | 40 |
| 3 | 8.96 | 6.72 | * |
| 4 | 8.96 | 6.72 | * |

*Observed safening effect was less than 19.

As noted previously, the 2-substituted-5-phenyl-4-thiazolecarboxylates may be used to protect sorghum from the herbicidal activity of triallate, alachlor and butachlor herbicides without a corresponding diminution in herbicidal activity to the weeds. Example 6 is illustrative of such activity.

EXAMPLE 6

A good grade of top soil was placed in a plastic pot and compacted to a depth of approximately 1.27 cm. from the top of said pot. A predetermined number of sorghum seeds and weed seeds were placed on top of the soil. A cover layer, approximately 1.27 cm., was placed on top of said seeds. The soil was then treated with a mixture of the safening agent and alachlor dispersed or dissolved in a suitable solvent. For each test series, pots were treated with only the herbicide. Additionally, pots were treated with only the safening agent. The herbicidal effect was observed approximately 21 days after treatment.

Table IV summarizes the results obtained when the compounds of the invention were tested in accordance with the procedure of Example 6. Table IV represents the results of different tests using this procedure. Note that in each test a control is used in which the sorghum plants are treated with various rates of alachlor herbicide alone.

TABLE IV

| Rate of Alachlor (kg/h) | Safening Agent* | Rate of Safening Agent (kg/h) | % Inhibition Sorghum | % Inhibition Green Foxtail |
|---|---|---|---|---|
| 0.56 | No Safening | 0 | 80 | 98 |
| 1.12 | Agent Present | 0 | 85 | 99 |

TABLE IV-continued

| Rate of Alachlor (kg/h) | Safening Agent* | Rate of Safening Agent (kg/h) | % Inhibition Sorghum | % Inhibition Green Foxtail |
|---|---|---|---|---|
| 2.24 | | 0 | 90 | 100 |
| 4.48 | | 0 | 95 | 100 |
| 0.00 | methyl 2-chloro-5-phenyl- | 8.96 | 0 | 0 |
| 0.56 | 4-thiazolecarboxylate | 8.96 | 30 | 100 |
| 1.12 | | 8.96 | 65 | 100 |
| 2.24 | | 8.96 | 70 | 100 |
| 4.48 | | 8.96 | 70 | 100 |
| 0.56 | No Safening | 0 | 80 | 98 |
| 1.12 | Agent Present | 0 | 85 | 98 |
| 2.24 | | 0 | 85 | 98 |
| 4.48 | | 0 | 100 | 100 |
| 0.00 | methyl 2-methoxy-phenyl- | 8.96 | 0 | 0 |
| 0.56 | 4-thiazolecarboxylate | 8.96 | 50 | 100 |
| 1.12 | | 8.96 | 65 | 100 |
| 4.48 | | 8.96 | 40 | 100 |
| | | 9.96 | 75 | 100 |

*The compound of Example 1 and Example 4 exhibited no significant safening when tested in accordance with the procedure of Example 6.

The above examples illustrate that the 2-substituted-5-phenyl-4-thiazolecarboxylates of the present invention are useful in reducing herbicidal injury to sorghum plants. The safening agents may be applied to the plant locus as a mixture, i.e., a mixture of a herbicidally effective amount of triallate, alachlor or butachlor and a safening effective amount of safening agent, or sequentially, i.e., the plant locus may be treated with an effective amount of triallate, alachlor or butachlor followed by a treatment with the safening agent or vice versa. The ratio of herbicide to safening agent may vary depending upon various factors, such as the weeds to be inhibited, mode of application, etc., but normally a herbicide to safening agent ratio ranging from 1:25 to 25:1, preferably 1:15 to 15:1, most preferably 1:10 to 10:1, parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared bt admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixtures thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixtures thereof in a liquid or particulate solid form can be carried out by conventional techniques utilizing, for example, spreaders, power dusters, boom and hand sprayers, spray dusters and granular applicators. The compositions can also be applied from airplanes as a dust or spray. If desired, application of the compositions of the invention to plants can be accomplished by incorporating the compositions in the soil or other media.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

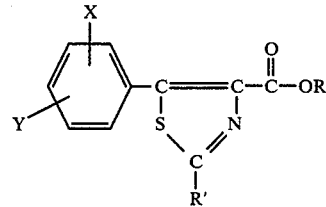

wherein R is hydrogen, lower alkyl, halo(lower)alkyl, lower alkenyl, halo(lower)alkenyl or agriculturally acceptable cations; R' is halo, amino, lower alkoxy or phenylthio. X and Y independently equal hydrogen, lower alkyl, lower alkoxy, trifluoromethyl or halo moieties; provided that when R is hydrogen or lower alkyl, R' may not equal amino.

2. A compound according to claim 1 wherein R is lower alkyl.

3. A compound according to claim 2 wherein R is methyl.

4. A compound according to claim 1 wherein R' is halo.

5. A compound according to claim 4 wherein R' is chloro.

6. A compound according to claim 1 wherein R' is amino.

7. A compound according to claim 1 wherein R' is lower alkoxy.

8. A compound according to claim 7 wherein R' is methoxy.

9. A compound according to claim 1 wherein X and Y are hydrogen.

10. A compound according to claim 1 wherein said compound is methyl 2-chloro-5-phenyl-4-thiazolecarboxylate or methyl 2-methoxy-5-phenyl-4-thiazolecarboxylate.

11. A method of reducing injury to sorghum plants due to application thereto of triallate, alachlor or butachlor herbicide which comprises applying to the plant locus a safening effective amount of a compound having the formula

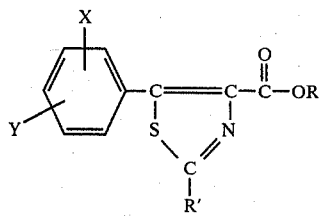

wherein R is hydrogen, lower alkyl, halo(lower)alkyl, lower alkenyl, halo(lower)alkenyl or agriculturally acceptable cations; R' is halo, amino, lower alkoxy or phenylthio; X and Y independently equal hydrogen, lower alkyl, lower alkoxy, trifluoromethyl or halo moieties.

12. A method according to claim 11 wherein R is lower alkyl.

13. A method according to claim 12 wherein R is methyl.

14. A method according to claim 11 wherein R' is halo.

15. A method according to claim 14 wherein R' is chloro.

16. A method according to claim 11 wherein R' is amino.

17. A method according to claim 11 wherein R' is lower alkoxy.

18. A method according to claim 17 wherein R' is methoxy.

19. A method according to claim 11 wherein X and Y are hydrogen.

20. A method according to claim 11 wherein said herbicide is alachlor.

21. A method according to claim 11 wherein said compound is methyl 2-chloro-5-phenyl-4-thiazole-carboxylate or methyl 2-methoxy-5-phenyl-4-thiazole carboxylate.

22. A mixture which comprises a herbicidally effective amount of triallate, alachlor or butachlor herbicide and a safening effective amount of a compound having the formula

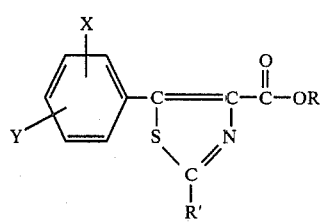

wherein R is hydrogen, lower alkyl, halo(lower)alkyl, lower alkenyl, halo(lower)alkenyl or agriculturally acceptable cations; R' is halo, amino, lower alkoxy or phenylthio. X and Y independently equal hydrogen, lower alkyl, lower alkoxy, trifluoromethyl or halo moieties.

23. A mixture according to claim 22 wherein R is lower alkyl.

24. A mixture according to claim 23 wherein R is methyl.

25. A mixture according to claim 22 wherein R' is halo.

26. A mixture according to claim 25 wherein R' is chloro.

27. A mixture according to claim 22 wherein R' is amino.

28. A mixture according to claim 22 wherein R' is lower alkoxy.

29. A mixture according to claim 28 wherein R' is methoxy.

30. A mixture according to claim 22 wherein X and Y are hydrogen.

31. A mixture according to claim 22 wherein said herbicide is alachlor.

32. A mixture according to claim 22 wherein said compound is methyl 2-chloro-5-phenyl-4-thiazole-carboxylate or methyl 2-methoxy-5-phenyl-4-thiazole carboxylate.

* * * * *